United States Patent [19]

Ciabatti et al.

[11] Patent Number: 4,496,743

[45] Date of Patent: Jan. 29, 1985

[54] 1-[(ACYLTHIOCYCLOALKYL)CARBONYL]-L-PROLINE DERIVATIVES

[75] Inventors: Romeo Ciabatti; Giovanna Padova, both of Milan, Italy

[73] Assignee: Gruppo Lepetit S.p.A., Milan, Italy

[21] Appl. No.: 460,972

[22] Filed: Jan. 26, 1983

Related U.S. Application Data

[62] Division of Ser. No. 239,941, Mar. 3, 1981, Pat. No. 4,385,062.

[30] Foreign Application Priority Data

Mar. 7, 1980 [GB] United Kingdom ................ 8007756

[51] Int. Cl.$^3$ ........................................... C07D 207/16
[52] U.S. Cl. .................................................. 548/533
[58] Field of Search ........................................ 548/533

[56] References Cited

U.S. PATENT DOCUMENTS

| 4,052,511 | 10/1977 | Cushman et al. | 548/533 X |
| 4,091,024 | 5/1978 | Ondetti | 548/533 X |
| 4,105,776 | 8/1978 | Ondetti et al. | 548/533 X |
| 4,108,886 | 8/1978 | Ondetti | 548/533 X |
| 4,297,282 | 10/1981 | Ohashi et al. | 548/533 |
| 4,385,062 | 5/1983 | Ciabatti et al. | 548/533 X |

FOREIGN PATENT DOCUMENTS 2072165 9/1981 United Kingdom ................ 548/533

OTHER PUBLICATIONS

Ondetti et al; Science, 196, (1977), pp. 441–444.
Harding et al.; J. Org. Chem.; 43, (1978), pp. 3974–3976.

*Primary Examiner*—Joseph Paul Brust
*Attorney, Agent, or Firm*—William J. Stein; Stephen L. Nesbitt; Gary D. Street

[57] ABSTRACT

This invention relates to 1-[(2-acylthiocycloalkyl)carbonyl]-L-proline derivatives which are useful as antihypertensive agents and to a process for their preparation.

3 Claims, No Drawings

1-[(ACYLTHIOCYCLOALKYL)CARBONYL]-L-PROLINE DERIVATIVES

This is a divisional of application Ser. No. 239,941, filed Mar. 3, 1981, now issued as U.S. Pat. No. 4,385,062.

The present invention relates to new 1-[(2-mercaptocycloalkyl)carbonyl]-L-proline derivatives, the process for their manufacture, the intermediates for their synthesis and their use as antihypertensive agents.

There is a continuous need for further developments of hypotensive agents since, even if significant advances in antihypertensive therapy have been achieved recently, an ideal antihypertensive agent is not available at the moment. L-proline, and thia(oxa)zolidine carboxylic acid derivatives useful as angiotensin converting enzyme inhibitors have been described recently in the open and patent literature (see for instance M. A. Ondetti et al., Science 196, 441–444 (1977), German Offenlegungsschrift No. 2,932,021, Belgian patent No. 879,158, and Japanese kokai No. 9060/80).

These compounds bear a mercapto- or substituted mercaptoalkanoyl group attached to the nitrogen atom of the heterocyclic moiety.

The new compounds which are the first object of the present invention are 1-[(2-mercaptocycloalkyl)carbonyl]-L-proline derivatives of the following general formula I

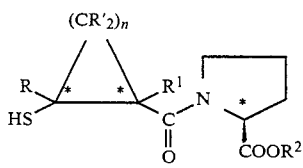

wherein R, $R^1$, and $R^2$, each independently, represent hydrogen or a $(C_{1-4})$alkyl radical, n represents the integer 1, 2, 3, 4, or 5, and, in each of the $n(CR'_2)$ groups $R'$ represents hydrogen or a $(C_1—C_4)$alkyl group.

The compounds of formula I possess three asymmetric centers which are indicated in the above formula by asterisks; however considering that the proline moiety has a fixed absolute configuration (the L configuration according to the standard Fischer convention) the compounds of formula I may exist in four diastereoisomeric forms: two cis diastereoisomers and two trans-diastereoisomers wherein "cis" and "trans" refer to the mutual position of the mercapto and carbonyl groups with respect to the plane of the cycloalkyl moiety.

More particularly, "trans-isomers" are those isomers wherein the

and the —SH groups lie trans to each other with respect to said plane, while cis isomers are those in which the above two groups lie cis to each other with respect to said plane. It is intended therefore that by referring to a [1-(2-mercaptocycloalkyl)carbonyl]-L-proline derivative of formula I, either the single pure diastereoisomers or any mixture thereof are encompassed by the present application.

The novel compounds of the present invention are useful in the treatment of hypertension.

A second object of the present invention is the process for preparing the novel compounds of formula I which is schematically described in the following chart.

Chart I

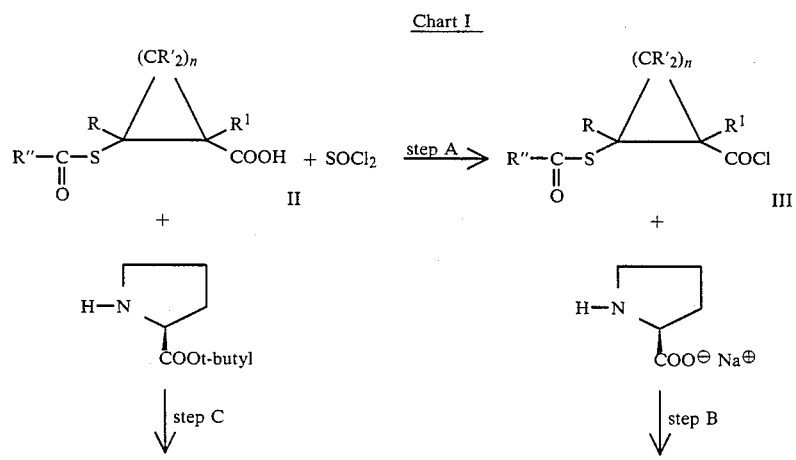

-continued
Chart I

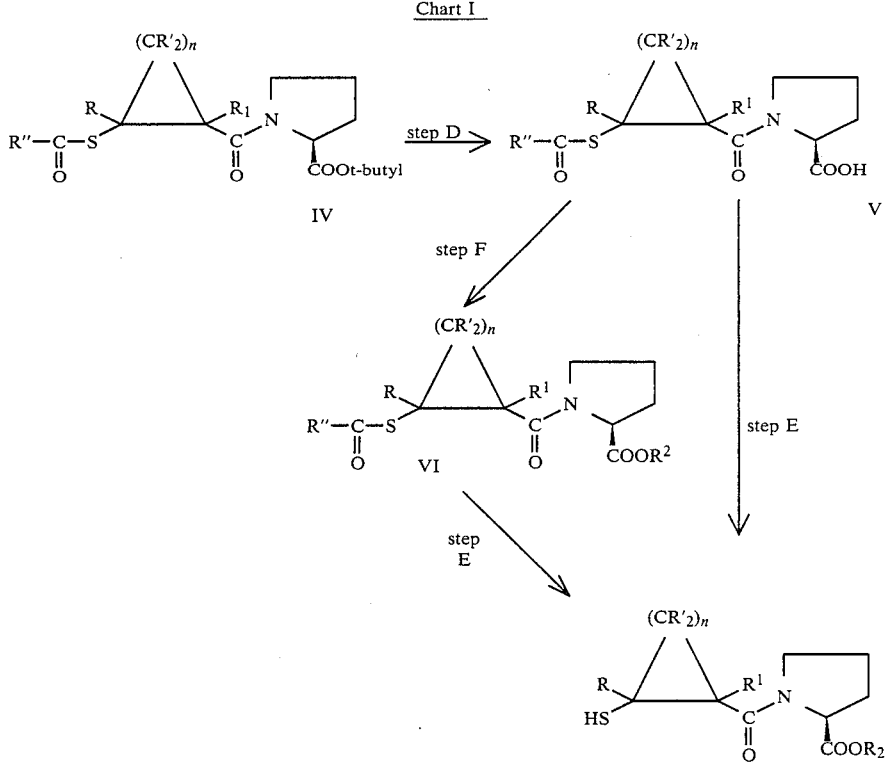

According to step A above a compound of formula II wherein R, R', R¹, and n are as defined before and R" is a methyl or phenyl group is reacted with thionyl chloride under conditions which are commonly employed in organic chemistry for the formation of acyl chlorides from acids. Thus a slight excess of thionyl chloride is added at low temperature generally comprised between 0° and 5° C., to the compound of formula II and once the reaction is completed the excess thionyl chloride is removed. The acyl chloride III is then isolated by distillation under reduced pressure and employed in the subsequent step—step B—which comprises the reaction with L-proline sodium salt.

This reaction is carried out in water, at low temperatures and requires the presence of an acid acceptor agent. As acid acceptor agents, inorganic bases or tertiary organic nitrogen bases, such as sodium or potassium carbonate or hydroxide trimethyl- or triethylamine, pyridine, picoline, and the like can suitably be employed; however better results can be achieved by using a further amount of L-proline sodium salt to act as hydrochloric acid acceptor. Thus according to a preferred embodiment, the acyl chloride III is gradually added to a solution of at least a double molar amount of L-proline dissolved in the stoichiometric amount of 1N NaOH. The reaction mixture is maintained at 0°–5° C. for the time of the addition then the temperature is allowed to increase to the room value. Once the reaction which is followed by thin layer chromatography, is completed, the compound V is isolated from the reaction mixture by common procedures which include acidification with a strong mineral acid, such as sulfuric or hydrochloric acid, and extraction with an inert organic solvent, preferably diethyl ether. The product thus obtained may be purified according to conventional procedures, such as crystallization from a suitable solvent, column chromatography or both techniques.

Alternatively, according to step C, the starting acid of formula II is reacted directly with L-proline t-butyl ester in the presence of a coupling agent to give the amide IV. Several coupling agents, such as for instance dicyclohexylcarbodiimide, N,N'-carbonyldiimidazole, N-ethoxycarbonyl-2-ethoxy-1,2-dihdyroquinoline and the like, may be employed in this reaction, however the use of dicyclohexylcarbodiimide is preferred. The reaction is carried out in the presence of an inert organic solvent such as benzene, chlorobenzene, toluene, chlorinated lower hydrocarbons and the like and preferably methylene chloride, at a temperature comprised between about 0° C. and the room value and preferably about 0° C. Once the reaction is completed, conventional working up of the reaction mixture gives the ester IV which is converted into the intermediate V by cleavage of the tert-butyl ester with $CF_3COOH$.

Finally, deprotection of the thiolester V yields the corresponding compound of formula I wherein $R_2$ is hydrogen. Depending on the meanings of R" deprotection is achieved by following different procedures which are however entirely familiar to the skilled technician. More particularly, when R" is methyl, the best results are obtained by base-catalyzed alcoholysis of the thiolester V using a lower alkanol, i.e. methanol or ethanol, and sodium or potassium hydroxide or carbonate as the basic catalyst, while when R" is phenyl, treatment with aqueous ammonia is preferred.

When compounds of formula I are desired wherein $R^2$ is a lower alkyl group, they may be prepared starting from the thiolester V by means of conventional esterification procedures followed by deprotection of the obtained intermediate of formula VI through transesterification with $K_2CO_3/R^2OH$.

The intermediates of formula V and of formula VI which share the same kind of pharmacological activity of the final compounds I, represent a further specific object of the present invention.

Analogously to the end compounds I also the intermediates V, as well as the intermediates VI, may exist in four diastereoisomeric forms, the above formulas V, and VI are therefore intended to represent either the single pure diastereoisomers or any mixture thereof. If trans or cis products of formula I (or V or VI) or the single isomers are desired, it is preferable to carry out the process as described in Chart I above but starting from a single couple of enantiomers (cis or trans) of formula II. In this case, starting from a single couple of enantiomers (cis or trans) of formula II, owing to the reaction with the optically active base, L-proline, the intermediates IV and V, as well as the end product I are obtained as mixtures of two cis or trans diastereoisomers which, if desired, may be separated into the single components.

Considering that diastereoisomers possess different chemico-physical properties, this separation can be easily achieved by means of conventional procedures known in chemistry to this purpose such as for instance fractional crystallization from a suitable solvent or chromatographic techniques. Alternatively if the single diastereoisomers of formula I (or V or VI) are desired, it may be convenient, once the starting acid of formula II is separated into the two couples of enantiomers, to react each single couple with an optically active base, separate the two diastereoisomers which form, separately restore the free acid and further process it as described in Chart I.

The starting compounds of formula II may be prepared by different methods depending on the meanings of $R^1$, R and n. More particularly, when n is the integer 2, 3, 4, or 5 and $R^1$ is hydrogen, the starting acid of formula II is prepared by reacting the corresponding 1-cycloalkene-1-carboxylic acid or 2-($C_1$–$C_4$)alkyl-1-cycloalkene-1-carboxylic acid with an excess of thioacetic or thiobenzoic acid (R"=methyl or phenyl respectively), which adds to the double bond yielding a compound II wherein $R^1$ is hydrogen, n is the integer 2, 3, 4, or 5, R is hydrogen or a ($C_1$–$C_4$)alkyl group and R" is methyl or phenyl.

The reaction may be carried out in the absence or in the presence of a solvent. In this latter case an aprotic, polar or non-polar, organic solvent which does not interfere with the addition reaction should be employed.

Representative examples of suitable solvents are dimethylsulfoxide, dimethylformamide, chlorobenzene, chlorinated lower hydrocarbons, benzene and the like.

The reaction is preferably carried out at a temperature between room temperature and the reflux temperature of the reaction mixture. The reaction rate increases with the temperature and in general from about 1 to about 10 hours are sufficient for the reaction is completed.

In particular cases however a lower temperature could advantageously be employed provided a longer time is allowed. Once the reaction is terminated, the solvent, if any, and the excess of thioacid are boiled off and the residue is purified by chromatography.

In general the addition of the thioacid to the double bond leads to two diastereoisomeric couples of enantiomers, of which two are indicated as trans isomers since the —COOH, and —SCOR" groups lie trans to each other, and two as cis isomers for the above groups lie cis to each other. The ratio of cis to trans isomers resulting from the addition can not be predicted and depends on the structure of the starting 1-cycloalkene-1-carboxylic acid, on the thioacid and on the particular reaction conditions employed. In general it has been found that the addition is not stereospecific, since both isomers are obtained, but that it leads predominantly to the trans isomers. However, modification of the reaction conditions described above, such as a lower temperature, a prolonged reaction time, the use of a particular solvent and so on, may dramatically influence said ratio.

If a single couple of enantiomers (cis or trans) of formula II is desired, the mixture of the two diastereoisomeric couples of enantiomers thus obtained may be separated into trans and cis isomers by means of the usual procedures seen above.

When the fractional crystallization technique is employed better results are obtained by transforming the mixture of cis and trans acids of formula II into a cis-trans mixture of the corresponding salts with bulky bases, such as for instance dicyclohexylamine, separating the cis and trans salts and then restoring the free carboxy groups. By submitting the cis and trans isomers separately to the reaction steps A and B, or C and D, cis and trans isomers respectively of formula V are obtained which upon cleavage of the R"CO— group yield cis and trans products of formula I respectively. In their turn the starting 1-cycloalkene-1-carboxylic acids can be prepared from the corresponding cycloalkanones by a multistep process which involves reaction with an alkali metal cyanide, dehydration of the thus obtained cyanohydrin with $POCl_3$ in pyridine, followed by acid hydrolysis of the cyano group to carboxy. An alternative method comprises reduction of a 2-oxo-cycloalkyl carboxylic acid alkyl ester to the corresponding 2-hydroxycycloalkyl carboxylic acid alkyl ester by means of a suitable reducing agent, such as sodium borohydride, dehydration with $POCl_3$ in pyridine, and alkaline hydrolysis of the carbalkoxy group to carboxy.

When R stands for a ($C_1$–$C_4$)alkyl group, a modification of this latter method may suitably be employed for preparing the 2-($C_1$–$C_4$)alkyl-1-cycloalkene-1-carboxylic acids. More particularly, the starting 2-oxo-cycloalkyl carboxylic acid alkyl ester is reacted with $PCl_5$ to yield a 2-chloro-1-cycloalkene-1-carboxylic acid alkyl ester, which is then transformed into the corresponding 2-($C_1$–$C_4$)alkyl-1-cycloalkene-1-carboxylic acid alkyl ester by the action of a lithium-di-($C_1$–$C_4$)alkyl cuprate and finally, through alkaline hydrolysis of the carbalkoxy group, gives the desired 2-($C_1$–$C_4$)alkyl-1-cycloalkene-1-carboxylic acid.

These methods are known or are analogous to methods known in literature (see for instance J. Organic Chem. 43 3974 (1978) and the references cited therein).

Compounds of formula II wherein n is the integer 2,3,4, or 5, and $R^1$ is a ($C_1$–$C_4$)alkyl group can be prepared from 1-($C_1$–$C_4$)alkyl-2-hydroxy-cycloalkane carboxylic acids through reaction with thionyl chloride to give the corresponding 1-($C_1$–$C_4$)alkyl-2-chloro-cycloalkane carboxylic acid chlorides, alcoholysis of the obtained acyl chloride with t-butyl alcohol, reaction of the 1-($C_1$–$C_4$)alkyl-2-chloro-cycloalkane carboxylic acid t-butyl esters with thioacetic or thiobenzoic acid followed by cleavage of the t-butyl ester group. In their turn the 1-($C_1$–$C_4$)alkyl-2-hydroxy-cycloalkane carboxylic acids may be prepared from 2-oxo-cycloalkanecarboxylic acid lower alkyl esters through alkylation with R¹ I/NaH, followed by selective reduction of the keto group to hydroxy, and mild alkaline hydrolysis of the ester group to acid.

Finally, compounds of formula II wherein n is the integer 1 are prepared starting from propionic acid through addition of phenylmethanethiol followed by esterification of the acidic group with t-butylalcohol, cyclopropanation with $CH_2I_2/Zn-Cu$ according to the Simmons-Smith reaction, cleavage of the benzyl group by the use of liquid ammonia and sodium, according to the Birch reduction, reaction with benzoyl or acetyl chloride in pyridine and cleavage of the t-butyl ester with $CF_3COOH$.

Alternatively, compounds of formula II wherein n is the integer 1 can be prepared starting from an acrylic acid t-butyl ester of the formula $CR'_2=CR^1COO$ t-butyl wherein R' and R¹ are as previously defined, through photochemical cyclopropanation with $CHI_3$, followed by reaction of the obtained 2-iodo-cyclopropanecarboxylic acid t-butyl ester with thioacetic or thiobenzoic acid and cleavage of the t-butyl ester.

Alternatively, when separation of the diastereoisomers of the end compounds is not required, the intermediates of formula IV wherein n is the integer 2, 3, 4, or 5 can be prepared starting from 2-oxo-1-($C_1$-$C_4$)alkyl-cycloalkane carboxylic acid lower alkyl esters, through selective reduction of the keto group to hydroxy, saponification of the ester group to carboxy, acetylation of the hydroxy group with acetic anhydride in pyridine followed by condensation with L-proline t-butyl ester and reaction with the selected thioacid in alkaline medium.

As stated previously, a further specific object of the present invention is the use of the novel compounds of formula I as well as their intermediates of formula V and VI as antihypertensive agents, wherein with the term "use" all industrially applicable aspects and acts of said use are intended, including the embodying of the present compounds into pharmaceutical compositions.

At least in part the mechanism through which the new compounds of formula I and the intermediates of formula V and VI exert their antihypertensive activity is by inhibiting angiotensin converting enzyme.

In other words it has been shown that they inhibit the enzyme which transforms angiotensin I into the biologically active form, angiotensin II, which is the major vasoconstrictor component of the renal pressor system.

It is known from the pertinent literature in fact that angiotensin II acts directly on minute blood vessels causing contraction of aortic strips. In addition to this direct vasocostriction action which may be attributed to a direct effect on the smooth muscle or to an indirect effect mediated by liberation of norepinephrine from the sympathetic nerve endings, it is also known that angiotensin II, through stimulation of the adrenal glands, increases the concentration in blood of the potent mineralocorticoid, aldosterone. However, independently from the mechanisms through which angiotensin II participates in the elevation of blood pressure, the prevention of angiotensin II generation is of striking utility in the therapy of some kinds of hypertension. The activity of the compounds of the present invention as well as of the intermediates of formula V as converting enzyme inhibitors was ascertained both in vitro and in vivo. The in vitro activity was determined by a radioimmuno-assay carried out using the methodology illustrated by K. Poulsen in J. Lab. Clin. Med. 78, (2) pages 309–315 (1971). More particularly, the in vitro activity was quantitatively evaluated by following the procedure described below:

50 µl of rat plasma containing angiotensinogen, renin and converting enzyme in physiological amounts, but deprived of endogenous angiotensin-I and angiotensin-II, and 10 µl of angiotensin-II antibody in dilution (1:120) were incubated in a tube at 37° C. for 30 minutes.

During this enzymatic incubation in the absence of converting enzyme inhibitors, angiotensin-I which forms is then transformed into angiotensin-II by the action of converting enzyme and the angiotensin-II antibody which is present in the incubate, then captures and traps it, thus preserving angiotensin-II from the degrading action of plasmatic angiotensinases. Incubation was terminated by placing the tube at 0° C. and the amount of angiotensin-II formed and captured by the antibody was measured by radioimmunoassay (see K. Poulsen and J. Jörgensen J. Clin. Endocrinol. Metab. 39, 816–825 (1974).

The same general procedure as above, but incubating the rat plasma not only in the presence of the antibody but also in the presence of different concentrations of test compounds, was followed in order to evaluate the inhibitory activity of the test compounds on converting enzyme.

The assays, including also the control one, i.e. that carried out in the absence of test products, were performed simultaneously in order to ensure identical experimental conditions, which allow a correct comparison between the obtained results. As said above, the amount of captured angiotensin-II, was determined by a radioimmunological assay. In particular this determination was performed by adding 1 ml of a solution of labeled angiotensin-II (about 100 pg/1 ml) at 4° C. to all the tubes, and incubating at 4° C. for at least 18 hours, which is the minimum time interval for an equilibrium between labeled and unlabeled angiotensin-II and the antibody is reached. Free and antibody-bound angiotensin-II were then separated with 200 µl of dextran-coated charcoal. The charcoal, which had been previously placed in the plastic caps of each tube, was mixed simultaneously in all samples by turning the rack repeatedly upside-down during 30 seconds. After centrifugation at $3000\times g$ for 30 minutes the supernatant which contains the antibody-bound angiotensin-II, was decanted in counting tubes and each sample was then counted.

For calculation of generated angiotensin-II from the amount of antibody-bound labeled angiotensin-II, an angiotensin-II standard curve was constructed using 50 µg of standard angiotensin-II (containing zero to 7.5 pg of angiotensin-II) and 10 µl of angiotensin-II antibody in dilution (1:120). The same procedure as above, from the incubation at 37° C. for 30 minutes to the count of the antibody-bound labeled angiotensin-II, was followed, preferably simultaneously with the other assays. By plotting the amounts of antibody-bound labeled angiotensin-II versus the known amounts of angiotensin-II initially present, a standard curve can be constructed, which allow a direct correlation between the amount of antibody-bound labeled angiotensin-II determined in each test and the amount of generated angiotensin-II. By simple operations, the percent ihhibition of generation of angiotensin-II at different concentrations of tested compounds with respect to the control, can be calculated and an $IC_{50}$ (i.e. the concentration at which a 50% inhibition of formation of angiotensin-II with respect to the control occurs) may be derived. In representative experiments carried out as illustrated above the compounds of examples 2, 5B, and 6A showed an $IC_{50}$ of 0.57, 0.23, 0.21 μg/ml respectively.

In order to verify that the mechanism of action of the present compounds actually concerns the transformation of angiotensin-I to angiotensin-II and does not affect the generation of angiotensin-I, the same experiment was performed using 10 μl of angiotensin-I antibody in dilution (1:60) instead of angiotensin-II antibody. The experiment was carried out simultaneously with the above one and under the same conditions. The final count of the antibody-bound labeled angiotensin-I, not affected by the presence of the test compounds, demonstrated the specificity of action of the present compounds. The in vitro activity of the novel compounds as blockers of angiotensin converting enzyme was confirmed also in vivo by means of an experiment performed on normotensive rats under the following conditions: the animals, groups of three rats each, were anesthetized with nembuthal and fitted with two cannulas, one inserted in the carotid and connected to a pressure transducer for the recording of arterial blood pressure, and the other one inserted in the jugular vein for the intravenous injection of the challenging agent and of the substances to be tested.

The basal pressure value for each rat was recorded, then doses of 0.1 μg/Kg of body weight of angiotensin-I were injected through the jugular catheter. These doses produced an immediate and marked increase in blood pressure and the maximum values reached were recorded. From these values and the basal ones the pressure increase induced by angiotensin-I in each rat was calculated.

The test compounds were then administered at different doses to different groups of rats and after a time sufficient to allow the onset of action, generally 15 minutes, the angiotensin-I injections were repeated and the pressure recorded. The percentages of inhibition of the pressure increase induced by angiotensin-I by different doses of test compounds were easily calculated and for each dose a single value, averaged on the three animals of the group was considered. By plotting the concentrations of test compound on a logarithmic scale versus the percent inhibitory effects, a linear correlation was established which allowed the calculation of the $ED_{50}$, i.e. the dose of test compound which inhibits by 50% the pressure increase induced by angiotensin-I.

For the compound of examples 2, and 6B, the $ED_{50}$ values calculated as described above were 2.3 and 1.8 mg/kg respectively. Other in vivo experiments were performed in order to better evaluate the antihypertensive activity of the compounds of the present invention. More particularly these experiments were carried out on renal hypertensive dogs.

The methodology employed for production of this type of hypertension in the dog is that described by Goldblatt H. et al. in J. Exp. Med. 59, 347, (1934), through restriction of the renal artery.

The compounds to be tested were administered by the oral route to the conscious hypertensive animals in effective doses for seven consecutive days. The systolic arterial blood pressure was measured by the indirect method on the tail before and 1, 3, 5, and 7 hours after treatment. The results of these experiments showed that the compounds were effective in lowering the blood pressure. The drop of the systolic blood pressure ranged between 10 and 25% of the basal value, depending on the specific compound tested and on the time at which the blood pressure was observed. Moreover, with the compounds of the present invention the maximum blood pressure drop is reached through a gradual decrease which depending on the dose and the specific compound tested may take 2, 3 or even 6 days. As a consequence of this gradual lowering of the blood pressure to a normotensive level, all the circulatory parameters concerned are not dramatically affected by the antihypertensive action of the compounds of the present invention, and the undesired side-effects generally displayed by most of the known antihypertensive substances, are avoided.

The results obtained in these experiments show that the 1-[(2-mercaptocycloalkyl)carbonyl]-L-proline derivatives and the 1-[(2-acetyl and 1-(2-benzoyl-thiocycloalkyl)carbonyl]-L-proline derivatives of the present invention are useful in mammals for the treatment of certain kinds of hypertension.

Thus according to a further feature of the present invention, there are provided pharmaceutical compositions comprising a compound of formula I or a compound of formula V or VI as the active ingredient. In the exploitation of the invention the preferred routes of administration of the new compounds are the oral and the parenteral ones.

For oral administration the antihypertensive compounds of the present invention are compounded into pharmaceutical dosage forms such as for instance tablets, capsules, elixirs, solutions and the like, while parenterally administrable dosage forms are prepared as injectable ampoules. These pharmaceutical dosage forms are formulated as known in the art (see for instance Remington's Pharmaceutical Sciences 13$^{th}$ Ed., Mack Publishing Co., Easton, Pa.) and are prepared by common procedures. They may contain from about 100 to about 1000 mg of active ingredient. In addition to the therapeutical principle capsules and tablets may contain the usual pharmaceutically acceptable excipients, such as inert diluents, lubricating and disintegrating agents. Elixirs and solutions are prepared by dissolving the active ingredient in an aqueous or non aqueous pharmaceutically acceptable solvent and may contain also suspending, sweetening, flavoring and preservative agents as known in the art.

The dosage regimen for the compounds of the present invention in accord with an antihypertensive treatment will depend upon a variety of factors including the type, age and weight of the mammal. Good results can be obtained however by administering the compounds of the present invention, at a daily dosage range comprised between about 20 and 200 mg/kg preferably in divided doses. It is however clear that a daily dosage bejond the above indicated range may also be employed depending on the individual conditions of the subject to be treated.

The following examples which describe some of the compounds of the invention and the process for preparing them better illustrate the present invention, but are not to be construed as a limitation to its scope.

EXAMPLE 1

1-[(2-acetylthiocyclopentyl)carbonyl]-L-proline 19.5 g of (2-acetylthio)-cyclopentane carboxylic acid are dissolved in 8 ml of thionylchloride (12 g) keeping the temperature at 0° C. Once the addition is terminated the solution is allowed to stand at room temperature for 20 hours. Distillation under reduced pressure affords 18.5 g (91%) of [(2-acetylthio)cyclopentyl]carbonyl chloride. B.p. 130°–135° C./$_{4\text{-}2.8\ mm\ Hg}$.

16 g (0.0774 mole) of the acyl chloride obtained as described above are added dropwise to a solution of 18 g (0.156 mole) of L-proline in 156.5 ml (0.156 mole) of 1N NaOH. During the addition and for two further hours the temperature of the mixture is maintained around 5° C. After one night at room temperature the reaction mixture is cooled again annd acidified with concentrated hydrochloric acid to pH ~ 1.

By extracting with ethyl ether and then evaporating off the solvent 21 g of 1-[(2-acetylthio-cyclopentyl)carbonyl]-L-proline are recovered.

Preparation of the starting (2-acetylthio)-cyclopentane carboxylic acid

1$^{st}$ method: 10 g of sodium borohydride are added to a solution of 62.4 g (0.4 mole) of 2-oxo-cyclopentylcarboxylic acid ethyl ester in 200 ml of methanol cooled to 0° C. When the reaction, which is followed by thin layer chromatography, is completed, the reaction mixture is poured with caution into an aqueous solution saturated with NaH$_2$PO$_4$. By extracting with ethyl ether and subsequently evaporating off the solvent, a residue is obtained which is purified by under vacuum distillation yielding 44 g of 2-hydroxy-cyclopentylcarboxylic acid ethyl ester (b.p. 87° C./$_{0.3\ mmHg}$).

3.2 g (0.02 mole) of this product are dissolved in 21 ml of pyridine and to this solution, cooled to 5° C., 3 ml of POCl$_3$ are gradually added. After 45 minutes, the reaction mixture is poured into ice/water and acidified with hydrochloric acid. By extracting with ethyl acetate and then evaporating off the solvent 2.3 g (82%) of 1-cyclopentene-1-carboxylic acid ethyl ester are obtained.

A solution of 2.3 g (0.0164 mole) of 1-cyclopentene-1-carboxylic acid ethyl ester, 1.3 g (0.032 mole) of NaOH, 50 ml of water, and 80 ml of methanol, is refluxed for about 20 minutes, then methanol is removed under vacuum and the aqueous solution is acidified with concentrated hydrochloric acid. On cooling 1.03 g of 1-cyclopentene-1-carboxylic acid precipitates. M.p. 120°–121° C.

6 ml of thioacetic acid are added to 2.24 g (0.02 mole) of 1-cyclopentene-1-carboxylic acid.

The reaction mixture is heated to the reflux temperature for about 1 hour and then allowed to stand at room temperature for one night. The excess of thioacetic acid is boiled off under vacuum and the residue is purified by column chromatography using a silica gel column previously washed with hydrochloric acid and eluting with a mixture of petroleum ether and increasing volumes of ethyl ether. 2.5 g (66%) of (2-acetylthio)cyclopentane carboxylic acid are recovered. By carrying out the reaction under the same conditions but prolonging heating to 8 hours, the final compound is obtained in 81% yield.

2$^{nd}$ method: a solution of 69 g (0.363 mole) of sodium pyrosulfite in 180 ml of water is added dropwise to a mixture of 30 g (0.357 mole) of cyclopentanone 48 g (0.738 mole) of potassium cyanide and 150 ml of water cooled to −10°–15° C. by means of a mixture ice/sodium chloride and vigorously stirred. Then the temperature is allowed to increase to the room value and the reaction mixture is stirred for further four hours. By extracting with ethyl ether, and then evaporating off the solvent, 39 g (0.35 mole) of cyanohydrin are obtained.

A mixture of 90 ml of POCl$_3$ in 90 ml of pyridine is dripped into a solution of the cyanohydrin obtained above in 75 ml of benzene and 75 ml of pyridine. Once the addition is terminated the reaction mixture is refluxed for 30 minutes, then cooled and poured into ice/water. The mixture is extracted with ethyl ether, and the organic extracts are washed with 10% hydrochloric acid and then with water. The organic solvent is removed and 31.7 g of raw product are recovered which by distillation under reduced pressure give 25 g of 1-cyano-1-cyclopentene.

18 g of this product are refluxed for 6 hours with 60 ml of 85% H$_3$PO$_4$. The reaction mixture is cooled, diluted with 60 ml of water and saturated with NaCl.

The aqueous mixture is extracted with ethyl ether, the organic extracts are combined and washed with an aqueous solution saturated with NaCl. By evaporating off the solvent and crystallizing the obtained residue from pentane, 4.7 g of 1-cyclopentene-1-carboxylic acid (m.p. 120°–121° C.) are recovered.

The addition of thioacetic acid to the 1-cyclopentene-1-carboxylic acid thus obtained is carried out as described in the first method.

EXAMPLE 2

1-[(2-mercaptocyclopentyl)carbonyl]-L-proline

A mixture of 100 ml of anhydrous methanol and 100 ml of ammonia saturated anhydrous methanol, is added dropwise to a solution of 24.5 g (0.086 mole) of 1-[(2-acetylthiocyclopentyl)carbonyl]-L-proline in 50 ml of methanol cooled to 0° C. and maintained with stirring under nitrogen atmosphere. Once the addition is terminated the reaction mixture is stirred at room temperature under nitrogen for further four hours, then the solvent is evaporated and the residue is purified by column chromatography on Dowex 50 ® (a polystyrene sulfonated resin) eluting with distilled water. Yield: 18.5 g (88%) of 1-[(2-mercaptocyclopentyl)carbonyl]-L-proline with the following characteristics: $[\alpha]_D^{25} = -139.3°$ (C=1% in CHCl$_3$).

EXAMPLE 3

1-[(2-acetylthiocyclohexyl)carbonyl]-L-proline

By operating essentially as described in example 1 but starting from (2-acetylthio)cyclohexane carboxylic acid, 1-[(2-acetylthiocyclohexyl)carbonyl]-L-proline, as a mixture of four diastereoisomers, is obtained. The starting (2-acetylthio)cyclohexane carboxylic acid is prepared from cyclohexanone by following the procedure described under "2$^{nd}$ method" in example 1.

EXAMPLE 4

1-[(2-mercaptocyclohexyl)carbonyl]-L-proline

By following essentially the same procedures described in example 2 but starting from the compound of the foregoing example 1-[(2-mercaptocyclohexyl)carbonyl]-L-proline, as a mixture of four diastereoisomers, is obtained which has the following characteristics: $[\alpha]_D^{20°\ C.} = -114°$; (C=1% in CHCl$_3$).

EXAMPLE 5

1-[(2-benzoylthiocyclopentyl)carbonyl]-L-proline
(trans diastereoisomers)

(A) 6.85 g of L-proline t-butyl ester and 8.25 g of dicyclohexylcarbodiimide are dissolved with stirring in 55 ml of anhydrous methylene chloride. The solution is cooled to 0° C. and added with 10 g of trans (2-benzoyl-thio)cyclopentane carboxylic acid.

The reaction mixture is stirred at room temperature for one night and then filtered on a Büchner funnel. The solvent is evaporated and the residue is taken up with a small amount of methylene chloride and dried with a little magnesium sulfate.

The raw residue (18.28 g) obtained by evaporating off the solvent consists of a mixture of the two trans diastereoisomers of 1-[(2-benzoylthiocyclopentyl)carbonyl]-L-proline t-butyl ester and it is separated into the single components by preparative liquid chromatography (waters) eluting with a mixture ethyl acetate:hexane 1:3. The trans diastereoisomer which eluted first (8.0 g), here denominated 1-[(2-benzoylthiocyclopentyl)carbonyl]-L-proline t-butyl ester TUS (trans upper spot), melts at 73.5° C. (from hexane) and is characterized by $[\alpha]_D^{20} = -107.5°$ (C=1.03% in CHCl$_3$) while the other trans diastereoisomer, denominated 1-[(2-benzoylthiocyclopentyl)carbonyl]-L-proline t-butyl ester TLS (trans lower spot), melts at 67° C. (from hexane), and is characterized by $[\alpha]_D^{20} = +4.8°$ (C=0.98% in CHCl$_3$). A different crystalline form, obtained by grinding the above compound in a mortar, melted at 79° C.

(B) A solution of methoxy benzene (53 ml) and trifluoroacetic acid (77 ml) is added to 1-[(2-benzoylthiocyclopentyl)carbonyl]-L-proline t-butyl ester TUS and the reaction mixture is allowed to stand at room temperature for about 2 hours, then the reaction mixture is brought to dryness at the pump heating to about 35° C. The residue is dissolved in ethyl acetate and extracted with saturated sodium bicarbonate solution. The aqueous phase is acidified with 10% HCl, salted with NaCl and extracted with ethyl acetate. The ethyl acetate is evaporated off and the obtained residue is dissolved in benzene/methylene chloride and dried again. This operation is repeated a few times in order to remove traces of trifluoro-acetic acid still present, then the residue is crystallized from ethyl acetate yielding one of the two trans diastereoisomers of 1-[(2-benzoylthiocyclopentyl)carbonyl]-L-proline (7 g) as a pure, unitary product having the following characteristics:

M.p. 105°–106° C.

$[\alpha]_D^{20} = -119.9°$ (C=0.99% in CHCl$_3$).

N.M.R. Spectrum recorded at 270 MHz in CDCl$_3$ (δ units): 1.7–2.6 (m, 10H, CH$_2$—CH$_2$); 3.08 (m, 1H, CHCO); 3.54 (m, 2H, CH$_2$N); 4.26 (d.t., 1H, $J_{CH-CH}=7.5$, $J_{CH-CH_2}=6.5$, CHS); 4.73 (m, 1H, COCH-N); 7.4–8.0 (m, 5H, CO-∅); 10.0–5.6 (b, 1H, COOH) [m=multiplet; d.t.=doublet of triplets; b=broad].

(C) By following the same procedure described above under (B) but starting from 1-[(2-benzoylthiocyclopentyl)carbonyl]-L-proline t-butyl ester TLS, the other trans diastereoisomer of 1-[(2-benzoylthiocyclopentyl)carbonyl]-L-proline, as a pure unitary product, is obtained having the following characteristics:

M.p. 88° C.

$[\alpha]_D^{20} = -81.8°$.

N.M.R. Spectrum recorded at 270 MHz in CDCl$_3$ (δ units): 1.7–2.6 (m, 10H, CH$_2$—CH$_2$); 3.12 (d.t., 1H, $J_{CH-CH}=7.5$, $J_{CH-CH_2}=5.5$, CHCO); 3.4–3.8 (m, 2H, CH$_2$N); 4.23 (d.t., 1H, $J_{CH-CH_2}=7.5$, CH-S); 4.64 (m, 1H, CO—CH—N); 7.4–8.0 (m, 5H, CO∅); 11.0–6.5 (b, 1H, COOH).

Preparation of the starting trans (2-benzoylthio)cyclopentane carboxylic acid

A mixture of 21 g of 1-cyclopentene-1-carboxylic acid prepared as described in the second part of example 1 and 105 ml of thiobenzoic acid is heated to 120° C. on an oil bath under nitrogen stream for 7 hours.

After standing at room temperature for one night, the residue is purified by column chromatography using a silica gel column previously washed with hydrochloric acid and eluting with a mixture of petroleum ether and increasing volumes of ethyl ether. 26.5 g of a cis/trans 3:7 mixture of (2-benzoylthio)cyclopentane carboxylic acid is obtained which upon fractional crystallization from ethyl ether, yields 13.45 g of pure trans (12-benzoylthio)cyclopentane carboxylic acid; M.p. 100° C.

EXAMPLE 6

1-[(2-mercaptocyclopentyl)carbonyl]-L-proline (trans diastereoisomers)

(A) A solution of 24.7 ml of water and 16.2 ml of 32% NH$_4$OH is stirred into a 250 ml flask charged with 9 g of the trans diastereoisomer of 1-[(2-benzoylthiocyclopentyl)carbonyl]-L-proline with m.p. 105°–106° C. and $[\alpha]_D^{20} = -119°.9$ kept under Argon atmosphere.

When the addition is terminated stirring at room temperature is prolonged for 2 hours, then 100 ml of an aqueous solution saturated with NaCl is added and the benzamide which forms during the reaction is filtered off. The filtrate is washed with ethyl acetate, acidified with 10% HCl and extracted with ethyl acetate. The organic solvent is evaporated to dryness and the residue is crystallized from ethyl ether—Yield 4.35 g of one of the two trans-diastereoisomers of 1-[(2-mercaptocyclopentyl)carbonyl]-L-proline characterized by M.p. 117°–118° C.

$[\alpha]_D^{20} = -237.4°$ (C=1% in CHCl$_3$).

N.M.R. Spectrum recorded at 270 MHz in CDCl$_3$ (δ units): 1.5–2.4 (m, 10H, CH$_2$—CH$_2$); 1.79 (d, 1H,$J_{CH-SH}=8$, SH); 2.80 (d.t., 1H, $J_{CH-CH}=8$, $J_{CH-CH_2}=8$, CHCO); 3.4–3.8 (m, 3H, CH$_2$N+CHS); 4.62 (m, 1H, CO—CH—N); 8.38 (b.s., 1H, COOH).

(B) By operating substantially as described in part A above but starting from the trans diastereoisomer of 1-[(2-benzoylthiocyclopentyl)carbonyl]-L-proline characterized by m.p. 88° C. and $[\alpha]_D^{20} = -81.8°$, the other of the two trans diastereoisomers of 1-[(2-mercaptocyclopentyl)carbonyl]-L-proline is obtained.

This compound which is a unitary product, as evidentiated by differential scanning calorimetry, melts at 107°–109° C. and is characterized by $[\alpha]_D^{20} = -62.2°$ (C=1.02% in CHCl$_3$) and N.M.R. Spectrum recorded at 270 MHz in CDCl$_3$ (δ units): 1.5–2.5 (m, 10H, CH$_2$—CH$_2$); 1.94 (d, 1H, $J_{CH-SH}=8$, SH); 2.85 (d.t., 1H, $J_{CH-CH}=8$, $J_{CH-CH_2}=8$, CHCO); 3.52 (d.d.t., 1H, $J_{CH-CH_2}=8$, CHS); 3.5–4.0 (m, 2H, CH$_2$N); 4.60 (m,1H, CO—CH—N); 8.6–6.8 (b, 1H, COOH).

EXAMPLE 7

1-[(2-benzoylthiocyclopentyl)carbonyl]-L-proline (cis diastereoisomers)

(A) By operating essentially as described in example 5(A) but starting from cis (2-benzoylthio)cyclopentane carboxylic acid, the two cis diastereoisomers of 1-[(2-benzoylthiocyclopentyl)carbonyl]-L-proline t-butyl ester are obtained. The first eluted product here denominated 1-[(2-benzoylthiocyclopentyl)carbonyl]-L-proline t-butyl ester CUS (cis upper spot), melts at 80° C. (from hexane) and is characterized by $[\alpha]_D^{20} = -153.5°$ (C=1% in CHCl₃); while the other cis diastereoisomer, denominated 1-[(2-benzoylthiocyclopentyl)carbonyl]-L-proline t-butyl ester CLS (cis lower spot) melts at 68°-70° C. (from hexane) and is characterized by $[\alpha]_D^{20} = -2.7°$ (C=1% in CHCl₃).

(B) By following the procedures illustrated in example 5 part B) but starting from 1-[(2-benzoylthiocyclopentyl)carbonyl]-L-proline t-butyl ester CUS, (m.p. 80° C., $[\alpha]_D^{20} = -153.5°$) one of the two cis diastereoisomers of 1-[(2-benzoylthiocyclopentyl)carbonyl]-L-proline is obtained as a pure, unitary product having the following characteristics:

M.p. 152° C.
$[\alpha]_D^{20} = -183.4°$ (C=1.05% in CHCl₃).

N.M.R. Spectrum recorded at 270 MHz in CDCl₃ (δ units): 1.6-2.5 (m, 10H, CH₂—CH₂); 3.44 (d.t., 1H, $J_{CH-CH}=8$, $J_{CH-CH_2}=7.5$, CHCO); 3.59 (m, 2H, CH₂N); 4.27 (d.t., 1H, $J_{CH-CH_2}=8$, CHS); 4.49 (m, 1H, CO—CH—N); 7.4-8.0 (m, 5H, CO—∅); 9.5-5.5 (b, 1H, COOH).

(C) By operating essentially as described in example 5 part B) but starting from 1-[(2-(benzoylthiocyclopentyl)carbonyl]-L-proline t-butyl ester CLS (m.p. 68°-70° C., $[\alpha]_D^{20} = -2.7°$), the other of the two cis diastereoisomers of 1-[(2-benzoylthiocyclopentyl)carbonyl]-L-proline is obtained as an oily product having the following characteristics:

$[\alpha]_D^{20} = -59.7°$ (C=1.03% in CHCl₃).

N.M.R. Spectrum recorded at 270 MHz in CDCl₃ (δ units): 1.6-2.6 (m,10H, CH₂—CH₂); 3.4-3.7 (m, 3H, CH₂N+CHCO); 4.25 (d.t., 1H, $J_{CH-CH}=8$, $J_{CH-CH_2}=8$, CHS); 4.60 (m,1H, CO—CH—N); 7.4-8.0 (m, 5H, CO—∅); 8.6-5.1 (b, 1H, COOH).

Preparation of the starting cis (2-benzoylthio)cyclopentane carboxylic acid

The reaction between 1-cyclopentene-1-carboxylic acid and thiobenzoic acid is carried out as described in the portion headed "preparation of the starting trans (2-benzoylthio)cyclopentane carboxylic acid" of example 5.

Once the trans product is separated by fractional crystallization, the mother liquors deriving from the crystallization are evaporated to dryness and a slight excess of dicyclohexylamine in ethyl acetate is added to the obtained residue. The salification which is carried out under stirring at low temperature goes with almost quantitative yields. The obtained salt is recovered and crystallized from ethyl acetate (100 ml of ethyl acetate per gram of salt) yielding 8.8 g of pure cis (2-benzoylthio)cyclopentane carboxylic acid dicyclohexylamine salt (m.p. 175.5° C.). By suspending the above salt in 150 ml of ethyl acetate and adding to this suspension 70 ml of 5% NaHSO₄, 3.7 g of the corresponding free acid are obtained (m.p. 93.5° C.).

EXAMPLE 8

1-[(2-mercaptocyclopentyl)carbonyl]-L-proline (cis diastereoisomers)

(A) By operating substantially as described in example 6 part A) but starting from the cis diastereoisomer of 1-[(2-benzoylthiocyclopentyl)carbonyl]-L-proline with m.p. 152° C. and $[\alpha]_D^{20} = -183.4°$ one of the two cis diastereoisomers of 1-[(2-mercaptocyclopentyl)carbonyl]-L-proline is obtained as a pure, unitary product characterized by:

M.p. 89° C.
$[\alpha]_D^{20} = -149.6°$ (C=1.04% in CHCl₃).

N.M.R. Spectrum recorded at 270 MHz in CDCl₃ (δ units): 1.5-2.6 (m,10H, CH₂—CH₂); 1.65 (d,1H, $J_{CH-SH}=10$,SH); 3.1-3.4 (m,2H, CHCO+CHS); 3.62 (t, 2H, $J_{CH_2-CH_2}=7$, CH₂N); 4.67 (m, 1H, CO—CH—N); 8.8-5.7 (, 1H, COOH).

(B) By following the procedure described in example 6 part (A) but starting from the cis diastereoisomer of 1-[(2-benzoylthiocyclopentyl)carbonyl]-L-proline with $[\alpha]_D^{20} = -59.7°$, the other of the two cis diastereoisomers of 1-[(2-mercaptocyclopentyl)carbonyl]-L-proline is obtained as a pure, unitary product having the following characteristics:

M.p. 97° C.
$[\alpha]_D^{20} = -181.7°$.

N.M.R. Spectrum recorded at 270 MHz in CDcl₃ (δ units): 1.5-2.5 (m, 10H, CH₂—CH₂); 1.82 (d, 1H, $J_{CH-SH}=9$, SH); 3.18 (d.t., 1H, $J_{CH-CH}=7$, $J_{CH-CH_2}=7$, CHCO); 3.36 (d.d.t., 1H, $J_{CH-CH_2}=8$, CHS); 3.4-3.9 (m, 2H, CH₂N); 4.61 (m, 1H, CO—CHN); 9.00 (b.s., 1H, COOH).

EXAMPLE 9

1-[(2-benzoylthio-3,3-dimethyl-cyclopentyl)carbonyl]-L-proline(trans diastereoisomers)

(A) Trans 2-benzoylthio-3,3-dimethylcyclopentyl carboxylic acid (3.55 g) is added to a solution of L-proline tertbutyl ester (2.20 g) and dicyclohexylcarbodiimide (2.63 g) in anhydrous methylene chloride (18 ml) cooled to 0° C.

After stirring at 0° C. for 6 hours and at room temperature for 15 hours the mixture is filtered in order to eliminate the dicyclohexyl-urea which forms during the reaction and the filtrate is concentrated to dryness. The residue which is obtained is separated into the single trans components by preparative liquid chromatography eluting with hexane:ethyl acetate 7:3 Yield: 1.62 g of 1-[(2-benzoylthio-3,3-dimethyl-cyclopentyl]-L-proline tert-butyl ester TUS characterized by a m.p. of 170° C. and $[\alpha]_D^{20} = -82.5°$ (c=1.035% in CHCl₃) and 0.90 g of 1-[(2-benzoylthio-3,3-dimethyl-cyclopentyl)carbonyl]-L-proline t-butyl ester TLS characterized by m.p. 126° C. (from ethyl ether) and $[\alpha]_D^{20} = -34.6°$ (c=1.01% in CHCl₃).

(B) Anisole (40 ml) and trifluoro-acetic acid (65 ml) are added at room temperature to 1-[(2-benzoylthio-3,3-dimethylcyclopentyl)carbonyl]-L-proline t-butyl ester TUS (9.5 g). After standing at room teperature for 2 hours the reaction mixture is concentrated to dryness under vacuum at 35° C. The residue is taken up with ethyl ether and evaporated to dryness yielding 8.3 g of a white solid which is crystallized from ethyl acetate to give one of the two trans diastereoisomer of 1-[(2-benzoylthio-3,3-dimethyl-cyclopentyl)carbonyl]-L-proline as a unitary pure compound, m.p. 187° C., $[\alpha]_D^{20} = -90.5°$ (c=1.16% in CHCl₃).

(C) Anisole (40 ml) and trifluoroacetic acid (65 ml) are added to 1-[(2-benzoylthio-3,3-dimethyl-cyclopentyl)carbonyl]-L-proline t-butyl ester TLS (12.1 g). After standing at room temperature for 2½ hours the reaction mixture is brought to dryness at the pump at a temperature of 35° C.

The residue thus obtained is dissolved in ethyl acetate and extracted with aqueous NaHCO₃. The aqueous alkaline solution is acidified with 10% HCl, salted with NaCl and extracted with ethyl acetate. The organic phase is dried over MgSO₄ and concentrated to dryness and the residue is crystallized from ethyl ether yielding 7.75 g of the other of the two trans diastereoisomers of 1[(2-benzoylthio-3,3-dimethyl-cyclopentyl)carbonyl]-L-proline characterized by m.p. 153° C. and $[\alpha]_D^{20}=-141.2°$ (c=1.08% in CHCl$_3$).

Preparation of the starting trans 2-benzoylthio-3,3-dimethylcyclopentyl carboxylic acid.

A 1 l flask is charged with 2,2-dimethylcyclopentanone (33.6 g) and a few milliliters of dimethyl-carbonate and kept under nitrogen atmosphere. 65% sodium hydride (15.73 g) and dimethyl-carbonate (390 ml) are slowly added and the reaction mixture is heated to 80°–82° C. for 5 hours.

The reaction mixture is cooled to 0° C. and methanol (15 ml) and acetic acid (28 g) are added thereto. After standing one night at room temperature water (200 ml) is added and the reaction mixture is extracted with chloroform (3×120 ml). The chloroform phase is dried over MgSO$_4$ and chloroform is evaporated off yielding an oily residue of 2-oxo-3,3-dimethylcyclopentyl carboxylic acid methyl ester which is purified by distillation. B.P.$_{15\ mmHg}$105°–108°

A solution of 2-oxo-3,3-dimethylcyclopentyl carboxylic acid methyl ester (47.6 g) in methanol (150 ml) is added to a solution of citric acid (27.0 g) and NaOH (5.5 g) in water (300 ml). To the obtained mixture NaBH$_4$ (19.6 g) and citric acid (24 g) are gradually added and the temperature of the reaction is maintained between 18° and 23° C. while the pH is between 5 and 6.5.

When the reaction is completed, methanol is evaporated off under vacuum and the reaction mixture is extracted with methylene chloride. The methylene chloride phase is dried over Na$_2$SO$_4$ filtered and concentrated under vacuum yielding an oily residue of 2-hydroxy-3,3-dimethylcyclopentyl carboxylic acid methyl ester which is purified by distillation (B.P.0.8 65° C.) the obtained ester (33 g) is poured into a 1 liter flask containing KOH (330 g). After 2 hours the mixture is heated on an oil bath to 180° C. for 2½ hours and then slowly cooled to 0° C. Water (700 ml) is added and the obtained solution is cooled to 0°–10° C. and acidified with concentrated HCl.

By filtering at 0°–10° C. and washing the solid on filter with cold water (200 ml), 3,3-dimethyl-1-cyclopentene-carboxylic acid (2.5 g) is obtained which melts at 67°–69° C. (from water).

A mixture of 3,3-dimethyl-1-cyclopentene-1-carboxylic acid (2 g) and thio-benzoic acid (2.37 g) is heated to 120° C. for 14 hours under Argon stream. The reaction mixture is cooled, taken up with a small amount of cyclohexane and filtered yielding 2.05 g of trans 2-benzoylthio-3,3-dimethylcyclopentyl carboxylic acid. M.p. 131° C. (from hexane)

From the mother liquors, concentrated to dryness, a cis/trans mixture of 2-benzoylthio-3,3-dimethylcyclopentyl carboxylic acid is recovered which is separated into the cis and trans enantiomers by column chromatography.

EXAMPLE 10

1-[(2-mercapto-3,3-dimethyl-cyclopentyl)carbonyl]-L-proline (trans diastereoisomers)

(A) 81 ml of water and 54 ml of 32% NH$_4$OH are added under stirring to 5.25 g of the trans diastereoisomer of 1-[(2-benzoylthio-3,3-dimethyl-cyclopentyl)carbonyl]-L-proline characterized by m.p. 187° C., kept under Argon atmosphere, and the reaction mixture is allowed to stand at room temperature for 2 hours.

When the reaction, which is followed by thin layer chromatography, is completed the reaction mixture is extracted with methylene chloride, acidified with hydrochloric acid, salted with NaCl and extracted with ethyl acetate. The organic solvent is boiled off and the residue is dissolved again in ethyl acetate and extracted with aqueous NaHCO$_3$. The aqueous alkaline phase is salted and extracted with ethyl acetate until benzamide which formed during the reaction is completely removed. The aqueous phase is then acidified with hydrochloric acid and extracted with ethyl acetate. By evaporating off the solvent a residue is obtained which is crystallized from ethyl ether yielding 2.5 g of one of the two trans diastereoisomers of 1-[(2-mercapto-3,3-dimethyl-cyclopentyl)carbonyl]-L -proline, as a pure unitary product characterized by m.p. 139° C. and $[\alpha]_D^{20}=-132.8°$ (c=1.01% in CHCl$_3$).

(B) Water (27 ml) and 32% NH$_4$OH (18 ml) are added to the trans diastereoisomer of 1-[(2-benzoylthio-3,3-dimethylcyclopentyl)carbonyl]-L-proline (5.25 g) characterized by m.p. 153° C. kept under Argon atmosphere. The reaction mixture is stirred at room temperature for 2½ hours then an aqueous solution saturated with (NH$_4$)$_2$SO$_4$ (45 ml) is added and the mixture is stirred at 0°–5° C.

After 30 minutes the reaction mixture is filtered at the pump and the filtrate is washed with ethyl acetate. The aqueous solution is acidified with 10% HCl and extracted with ethyl acetate. The organic solvent is evaporated off and the residue is crystallized from ethyl ether yielding 3.05 g of the other of the two trans diastereoisomers of 1-[(2-mercapto-3,3-dimethylcyclopentyl)carbonyl]-L-proline which has the following characteristics: m.p. 147° C. $[\alpha]_D^{20}=-63.7°$ (c=1.055% in CHCl$_3$).

EXAMPLE 11

1-[(2-benzoylthio-3,3-dimethylcyclopentyl)carbonyl]-L-proline (cis diastereoisomers)

By operating essentially as described in example 9 but starting from cis 2-benzoylthio-3,3-dimethylcyclopentyl carboxylic acid the two cis diastereoisomers of 1-[(2-benzoylthio-3,3-dimethylcyclopentyl)carbonyl]-L-proline are obtained.

EXAMPLE 12

1-[(2-mercapto-3,3-dimethylcyclopentyl)carbonyl]-L-proline (cis diastereoisomers)

By following the procedures described in example 10 but starting from the single cis diastereoisomers of 1-[(2-benzoylthio-3,3-dimethylcyclopentyl)carbonyl]-L-proline, the single cis diastereoisomers of 1-[(2-mercapto-3,3-dimethylcyclopentyl)carbonyl]-L-proline are obtained.

EXAMPLE 13

1-[(2-benzoylthiocyclobutyl)carbonyl]-L-proline (trans diastereoisomers)

(A) By operating essentially as described in example 5(A) but starting from trans (2-benzoylthio)cyclobutane carboxylic acid, the single trans diastereoisomers of 1-[(2-benzoylthiocyclobutyl)carbonyl]-L-proline t-butyl ester are obtained; the trans diastereoisomer which eluted first, here denominated 1-[(2-benzoylthiocyclobutyl)carbonyl]-L-proline t-butyl ester TUS, melts at 102°–3° C. and is characterized by $[\alpha]_D^{20} = -138.8°$ (c=1% in CHCl$_3$) while the other trans diastereoisomer, denominated 1-[(2-benzoylthiocyclobutyl)carbonyl]-L-proline t-butyl ester TLS, melts at 112°-3° C. and is characterized by $[\alpha]_D^{20} = +12.7°$ (c=1.01% in CHCl$_3$).

(B) By following the procedure described in example 5(B) but starting from 1-[(2-benzoylthiocyclobutyl)carbonyl]-L-proline t-butyl ester TUS one of the two trans diastereoisomers of 1-[(-2-benzoylthiocyclobutyl)carbonyl]-L-proline is obtained which is characterized by m.p. 106°-7° C. and $[\alpha]_D^{20} = -119.6°$ (c=1.005% in CHCl$_3$).

(C) Starting from 1-[(2-benzoylthiocyclobutyl)-L-proline t-butyl ester TLS (see (A) above) and operating as described in example 5(C), the other of the two trans diastereoisomers of 1-[(2-benzoylthiocyclobutyl)carbonyl]-L-proline is obtained which has the following characteristics: m.p. 123°-4° C., $[\alpha]_D^{20} = -86.33°$ (c=0.995% in CHCl$_3$).

Preparation of the starting trans (2-benzoylthio)cyclobutane carboxylic acid.

A mixture of 1-cyclobutene-1-carboxylic acid (2.8 g) and thiobenzoic acid (5.6 ml) is heated to 120° C. under Argon stream.

After 6 hours the reaction mixture is cooled, taken up with a small amount of cyclohexane and filtered. The filtrate is concentrated to dryness and the obtained residue is purified by Silica Gel column chromatography eluting with petroleum ether containing 15% of ethyl ether. Yield 1.05 g of pure trans (2-benzoylthio)cyclobutane carboxylic acid. M.p. 106°-7° C. (from ethyl ether).

By using an eluting system containing a lower percentage of ethyl ether, cis (2-benzoylthio)cyclobutane carboxylic acid is recovered.

EXAMPLE 14

1-[(2-mercaptocyclobutyl)carbonyl]-L-proline (trans diastereoisomers)

(A) By following the procedure described in example 6(A) but starting from the compound of example 13(B), one of the two trans distereoisomers of 1-[(2-mercaptocyclobutyl)carbonyl]-L-proline is obtained which has the following characteristics:

m.p. 145°-6° C. and $[\alpha]_D^{20} = -192.3°$ (c=1.065% in CHCl$_3$).

(B) By operating substantially as described in example 6(A) but starting from the compound of example 13(C), the other of the two trans diastereoisomers of 1-[(2-mercaptocyclobutyl)carbonyl]-L-proline is obtained which is characterized by: m.p. 137°-8° C. and $[\alpha]_D^{20} = -44.16°$ (C=0.985% in CHCl$_3$).

EXAMPLE 15

1-[(2-benzoylthiocyclobutyl]-L-proline (cis diastereoisomers)

By operating as described in example 5 but starting from cis (2-benzoylthio)cyclobutane carboxylic acid the two single cis diastereoisomers of 1-[(2-benzoylthiocyclobutyl)carbonyl]-L-proline are obtained.

EXAMPLE 16

1-[(2-mercaptocyclobutyl)carbonyl]-L-proline (cis diastereoisomers)

By following the procedure described in example 6 but starting from the two single cis diastereoisomers of 1[(2-benzoylthiocyclobutyl)carbonyl]-L-proline, the two cis diastereoisomers of 1[(2-mercaptocyclobutyl)carbonyl]-L-proline are obtained.

By following essentially the same procedures described in the foregoing examples the following compounds are obtained:

1-[(2-mercapto-2-methylcyclopentyl)carbonyl]-L-proline (trans diastereoisomers)

1-[(2-mercapto-2-methylcyclopentyl)carbonyl]-L-proline (cis diastereoisomers)

1-[(2-benzoylthio-2-methylcyclopentyl)carbonyl]-L-proline (trans diastereoisomers)

1-[(2-benzoylthio-2-methylcyclopentyl)carbonyl]-L-proline (cis diastereoisomers)

1-[(2-benzoylthio-3,3-diethylcyclopentyl)carbonyl]-L-proline (trans diastereoisomers)

1-[(2-benzoylthio-3,3-diethylcyclopentyl)carbonyl]-L-proline (cis diastereoisomers)

1-[(3,3-diethyl-2-mercaptocyclopentyl)carbonyl]-L-proline (trans diastereoisomers)

1-[(3,3-diethyl-2-mercaptocyclopentyl)carbonyl]-L-proline (cis diastereoisomers)

1-[(2-benzoylthio-3,3-dibutylcyclopentyl)carbonyl]-L-proline (trans diastereoisomers)

1-[(2-benzoylthio-3,3-dibutylcyclopentyl)carbonyl]-L-proline (cis diastereoisomers)

1-[(3,3-diethyl-2-mercapto-cyclopentyl)carbonyl]-L-proline (trans diastereoisomers)

1-[(3,3-diethyl-2-mercapto-cyclopentyl)carbonyl]-L-proline (cis diastereoisomers)

1-[(2-benzoylthio-3,3-dipropylcyclopentyl)carbonyl]-L-proline (trans diastereoisomers 1-[(2-benzoylthio-3,3-dipropylcyclopentyl)carbonyl]-L-proline (cis diastereoisomers)

1-[(2-mercapto-3,3-dipropylcyclopentyl)carbonyl]-L-proline (trans diastereoisomers)

1-[(2-mercapto-3,3-dipropylcyclopentyl)carbonyl]-L-proline (cis diastereoisomers)

1-[(2-benzoylthio-3,3-dimethylcyclopropyl)carbonyl]-L-proline (trans diastereoisomers)

1-[(2-benzoylthio-3,3-dimethylcyclopropyl)carbonyl]-L-proline (cis diastereoisomers)

1-[(2-mercapto-3,3-dimethylcyclopropyl)carbonyl]-L-proline (trans diastereoisomers)

1-[(2-mercapto-3,3-dimethylcyclopropyl)carbonyl]-L-proline (cis diastereoisomers)

1-[(2-benzoylthiocyclopropyl)carbonyl]-L-proline (trans diastereoisomers)

1-(2-benzoylthiocyclopropyl)carbonyl]-L-proline (cis diastereoisomers)

1-[(2-mercaptocyclopropyl)carbonyl]-L-proline (trans diastereoisomers)

1-[(2-mercaptocyclopropyl)carbonyl]-L-proline (cis diastereoisomers)

1-[(2-mercapto-1-methylcyclopentyl)carbonyl]-L-proline (trans diastereoisomers)

1-[(2-mercapto-1-methylcyclopentyl)carbonyl]-L-proline (cis diastereoisomers)

1-[(2-benzoylthio-1-methylcyclopentyl)carbonyl]-L-proline (trans diastereoisomers)

1-[(2-benzoylthio-1-methylcyclopentyl)carbonyl]-L-proline

1-[(2-benzoylthio-1-ethylcyclopentyl)carbonyl]-L-proline (trans diastereoisomers)

1-[(2-benzoylthio-1-ethylcyclopentyl)carbonyl]-L-proline (cis diastereoisomers)

1-[(1-ethyl-2-mercaptocyclopentyl)carbonyl]-L-proline (trans diastereoisomers)

1-[(1-ethyl-2-mercaptocyclopentyl)carbonyl]-L-proline (cis diastereoisomers)

1-[(1-isopropyl-2-mercaptocyclopentyl)carbonyl]-L-proline (trans diastereoisomers)

1-[(1-isopropyl-2-mercaptocyclopentyl)carbonyl]-L-proline (cis diastereoisomers)

1-[(2-benzoylthio-1-isopropylcyclopentyl)carbonyl]-L-proline (trans diastereoisomers)

1-[(2-benzoylthio-1-isopropylcyclopentyl)carbonyl]-L-proline (cis diastereoisomers)

We claim:

1. A compound of the formula

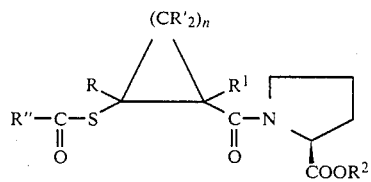

wherein R, $R^1$, and $R^2$, each independently, represent hydrogen or a ($C_1$–$C_4$)alkyl radical, R" stands for methyl or phenyl, n represents the integer 1, 2, 3, 4, or 5 and in each of the n ($CR'_2$) groups R' represents hydrogen or a ($C_1$–$C_4$)alkyl group.

2. A compound of claim 1 wherein the carbonyl and the acylthio groups lie trans to each other with respect to the plane of the cycloalkyl moiety.

3. A compound of claim 1 which is the 1-[(2-benzoylthiocyclopentyl)carbonyl]-L-proline.

* * * * *